United States Patent
Massaro et al.

(10) Patent No.: US 10,779,521 B2
(45) Date of Patent: Sep. 22, 2020

(54) AUTOMATED MASS REARING SYSTEM FOR INSECT LARVAE

(71) Applicant: Verily Life Sciences LLC, South San Francisco, CA (US)

(72) Inventors: Peter Massaro, Belmont, CA (US); Robert Sobecki, Mountain View, CA (US); Charles Behling, Mountain View, CA (US); Victor Criswell, Mountain View, CA (US); Tiantian Zha, Mountain View, CA (US); Roman Devengenzo, San Jose, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 279 days.

(21) Appl. No.: 15/716,981

(22) Filed: Sep. 27, 2017

(65) Prior Publication Data

US 2018/0092339 A1 Apr. 5, 2018

Related U.S. Application Data

(60) Provisional application No. 62/404,372, filed on Oct. 5, 2016.

(51) Int. Cl.
*A01K 67/033* (2006.01)
*G06Q 50/02* (2012.01)
*A01K 29/00* (2006.01)

(52) U.S. Cl.
CPC .......... *A01K 67/033* (2013.01); *G06Q 50/02* (2013.01); *A01K 29/00* (2013.01)

(58) Field of Classification Search
CPC ...... A01K 67/033; A01K 1/031; A01K 29/00; A01K 1/0236; A01K 1/0245; A01K 29/005; A01K 5/00; A01K 61/54; A01K 67/04

(Continued)

(56) References Cited

U.S. PATENT DOCUMENTS 3,223,237 A 12/1965 Stevens et al.
3,468,289 A 9/1969 Broida
(Continued)

FOREIGN PATENT DOCUMENTS

CN 102499182 6/2012
CN 202285912 7/2012
(Continued)

OTHER PUBLICATIONS

U.S. Appl. No. 15/285,623, Notice of Allowance dated Apr. 16, 2018, 9 pages.
(Continued)

*Primary Examiner* — Yvonne R Abbott-Lewis
(74) *Attorney, Agent, or Firm* — Kilpatrick Townsend & Stockton LLP

(57) ABSTRACT

Embodiments of the present disclosure can provide an automated mass rearing system for insect larvae. The automated mass rearing system can facilitate hatching, feeding, monitoring the growth and emergence of insect larvae and pupae. In some embodiments, the automated mass rearing system can include a production unit, a transportation unit, a storage unit, a dispensing unit, and a monitoring unit. In some embodiments, this automated mass rearing system can facilitate mass mosquito growth from egg hatching all the way through to full adults or certain stages in between such as the larvae rearing process (i.e., from larvae to pupae) with little or no human intervention. By automating the rearing and transportation of insect eggs, larvae, and pupae, deaths or developmental issues can be minimized. Various techniques and apparatuses are used in this automation that causes minimal disturbance to the insects during development, and thereby maximizing survival rate and fitness of the insects.

32 Claims, 5 Drawing Sheets

(58) Field of Classification Search
USPC .................................................. 119/6.5, 6.6
See application file for complete search history.

(56) References Cited

U.S. PATENT DOCUMENTS

| | | | |
|---|---|---|---|
| 3,750,625 A * | 8/1973 | Edwards .............. | A01K 67/033 |
| | | | 119/6.6 |
| 3,939,883 A * | 2/1976 | Harrell ..................... | B65B 3/32 |
| | | | 141/231 |
| 4,212,267 A * | 7/1980 | Patterson ............... | A01K 1/031 |
| | | | 119/6.5 |
| 4,368,690 A | 1/1983 | Tenzer | |
| 4,417,545 A | 11/1983 | Finney | |
| 4,646,683 A | 3/1987 | Maedgen, Jr. | |
| 4,765,275 A | 8/1988 | Yukawa et al. | |
| 4,785,764 A | 11/1988 | Mueller | |
| 4,863,693 A | 9/1989 | Howell | |
| 5,074,247 A | 12/1991 | Gupta et al. | |
| 5,178,094 A | 1/1993 | Carr et al. | |
| 5,241,778 A | 9/1993 | Price | |
| 5,351,643 A * | 10/1994 | Hughes ................ | A01K 67/033 |
| | | | 119/6.5 |
| RE35,348 E | 10/1996 | Georgi | |
| 5,594,654 A | 1/1997 | Shuman et al. | |
| 5,784,991 A | 7/1998 | Ukishiro et al. | |
| 5,819,685 A | 10/1998 | Kappelt et al. | |
| 6,244,213 B1 | 6/2001 | Tedders et al. | |
| 6,293,223 B1 | 9/2001 | Eberts et al. | |
| 6,474,259 B1 * | 11/2002 | Gaugler ............... | A01K 67/033 |
| | | | 119/6.7 |
| 6,557,487 B1 | 5/2003 | Fleischmann | |
| 6,653,971 B1 | 11/2003 | Guice et al. | |
| 6,688,255 B2 * | 2/2004 | Donaldson ........... | A01K 67/033 |
| | | | 119/6.5 |
| 6,766,251 B2 | 7/2004 | Mafra-Neto et al. | |
| 7,861,672 B2 * | 1/2011 | Power .................... | A01K 61/54 |
| | | | 119/236 |
| 8,322,304 B2 | 12/2012 | Chung | |
| 8,733,284 B2 * | 5/2014 | Courtright ........... | A01K 67/033 |
| | | | 119/6.6 |
| 9,295,245 B1 | 3/2016 | Guice et al. | |
| 9,510,572 B2 | 12/2016 | Aldana et al. | |
| 9,594,162 B1 | 3/2017 | Sonera et al. | |
| 9,642,344 B2 * | 5/2017 | Unger .................. | A01K 67/033 |
| 10,051,845 B1 | 8/2018 | Massaro et al. | |
| 2002/0035444 A1 | 3/2002 | Wilkerson et al. | |
| 2002/0185605 A1 | 12/2002 | Shuman et al. | |
| 2006/0196427 A1 * | 9/2006 | Lepori ................. | A01K 1/0245 |
| | | | 119/6.6 |
| 2007/0242566 A1 | 10/2007 | Hsu | |
| 2012/0017834 A1 | 1/2012 | Holland et al. | |
| 2012/0306683 A1 | 12/2012 | Viikari et al. | |
| 2013/0083974 A1 | 4/2013 | Tsai et al. | |
| 2013/0204581 A1 * | 8/2013 | Park ....................... | A01M 1/026 |
| | | | 702/188 |
| 2013/0319334 A1 * | 12/2013 | Newton ............... | A01K 67/033 |
| | | | 119/6.5 |
| 2014/0123902 A1 | 5/2014 | Kitazumi et al. | |
| 2016/0066552 A1 | 3/2016 | Arsiwalla et al. | |
| 2018/0042211 A1 | 2/2018 | Zamboni et al. | |
| 2018/0077912 A1 * | 3/2018 | Comparat ............ | A01K 67/033 |
| 2018/0206464 A1 | 7/2018 | Massaro et al. | |
| 2018/0206465 A1 | 7/2018 | Massaro et al. | |
| 2018/0206473 A1 | 7/2018 | Massaro et al. | |
| 2018/0279598 A1 | 10/2018 | Hur et al. | |

FOREIGN PATENT DOCUMENTS

| | | |
|---|---|---|
| CN | 105409893 | 3/2016 |
| WO | 2010038055 | 4/2010 |
| WO | 2015126855 | 8/2015 |
| WO | 2016024164 | 2/2016 |

OTHER PUBLICATIONS

Carvalho et al., "Mass production of genetically modified Aedes aegypti for field releases in Brazil", Journal of visualized experiments: JoVE 83 (2014).

International Application No. PCT/US2017/054094, "International Search Report and Written Opinion", dated Nov. 29, 2017, 12 pages.

U.S. Appl. No. 15/285,624, "Non-Final Office Action", dated Jan. 14, 2019, 10 pages.

U.S. Appl. No. 15/285,642, "Notice of Allowance", dated Jan. 23, 2019, 7 pages.

U.S. Appl. No. 15/285,866, "Notice of Allowance", dated Dec. 31, 2018, 7 pages.

U.S. Appl. No. 15/285,866, "Supplemental Notice of Allowance", dated Jan. 10, 2019, 2 pages.

U.S. Appl. No. 16/055,253, "Non-Final Office Action", dated Sep. 21, 2018, 6 pages.

U.S. Appl. No. 16/055,253, "Notice of Allowance", dated Jan. 10, 2019, 5 pages.

Liu et al., "A Review of Recent Sensing Technologies to Detect Invertebrates on Crops", Precision Agriculture, vol. 18, No. 4, Aug. 31, 2016, 38 pages.

Roberto et al., "Doppler Radar Signatures of Migrating Birds", Available online at https://ams.confex.com/ams/pdfpapers/21432.pdf https://ams.confex.com/ams/30radar/techprogram/paper_21432.htm, Jul. 20, 2001, 3 pages.

U.S. Appl. No. 15/285,642, "Non-Final Office Action", dated Aug. 9, 2018, 5 pages.

U.S. Appl. No. 15/285,624, "Final Office Action", dated May 6, 2019, 10 pages.

International Application No. PCT/US2017/054094, "International Preliminary Report on Patentability", dated Apr. 18, 2019, 10 pages.

U.S. Appl. No. 16/396,970, "Notice of Allowance", dated Feb. 26, 2020, 8 pages.

Balestrino et al., "A new larval tray and rack system for improved mosquito mass rearing", Journal of medical entomology, vol. 49, No. 3, May 2012, pp. 595-605.

U.S. Appl. No. 15/285,624, "Non-Final Office Action", dated Apr. 9, 2020, 8 pages.

EP17858927.1, "Extended European Search Report", dated Apr. 24, 2020, 7 pages.

* cited by examiner

AUTOMATED MASS REARING SYSTEM FOR INSECT LARVAE

CROSS-REFERENCE TO RELATED APPLICATIONS

The present application is related to and claims the benefit of priority of U.S. Provisional Application No. 62/404,372, filed Oct. 5, 2016, entitled "AUTOMATED MASS REARING SYSTEM FOR INSECT LARVAE", the entirety of which is incorporated herein by reference.

BACKGROUND

Mass rearing of mosquito larvae has conventionally been very labor intensive, requiring massive manpower. A lab technician may manually add a number of eggs or mosquito larvae to a plastic tray and determine the amount of food and water to add into the tray for the mosquito larvae. The lab technician may hand carry the plastic tray to a storage area to store the plastic tray. Periodically, the lab technician may perform observations on the mosquito larvae in the plastic tray and add food and water as needed. After the mosquito larvae evolve into pupae, the lab technician may segregate the females from the males using two glass plates. Not only are these processes very labor intensive, but also highly inaccurate when carried out by a person.

BRIEF SUMMARY

Various examples are described for automated insect rearing systems and methods. One disclosed system can include a larvae dispensing station having a first horizontal surface; a larvae dispenser comprising a larvae container and a larvae dispensing vessel, a first end of the larvae dispensing vessel coupled to a first orifice defined in the larvae container and a second end of the larvae dispensing vessel movable to be proximate to the first horizontal surface to dispense larvae from the larvae container at the first horizontal surface; a food dispensing station having a second horizontal surface; a food dispenser comprising a food container and a food dispensing vessel, a first end of the food dispensing vessel coupled to a second orifice defined in the food container and a second end of the food dispensing vessel movable to be proximate to the second horizontal surface to dispense food from the food container at the second horizontal surface; and a robotic storage system comprising at least one robotic arm and a shelf, the robotic arm configured to transfer a rearing container from the second horizontal surface to the shelf.

One disclosed method can include dispensing, by a larvae dispenser of an automated rearing system, larvae into a rearing container; dispensing, by a food dispenser of the automated rearing system, food for the larvae into the rearing container; transporting, by one or more robotic arms of the automated rearing system, the rearing container to a storage area of the automated rearing system; and monitoring, by one or more processors coupled to the automated rearing system, development of the larvae in the rearing container using one or more sensors in the storage area of the automated rearing system.

These illustrative examples are mentioned not to limit or define the scope of this disclosure, but rather to provide examples to aid understanding thereof. Illustrative examples are described in the Detailed Description, which provides further description. Advantages offered by various examples may be further understood by examining this disclosure.

DETAILED DESCRIPTION

Figure 1:
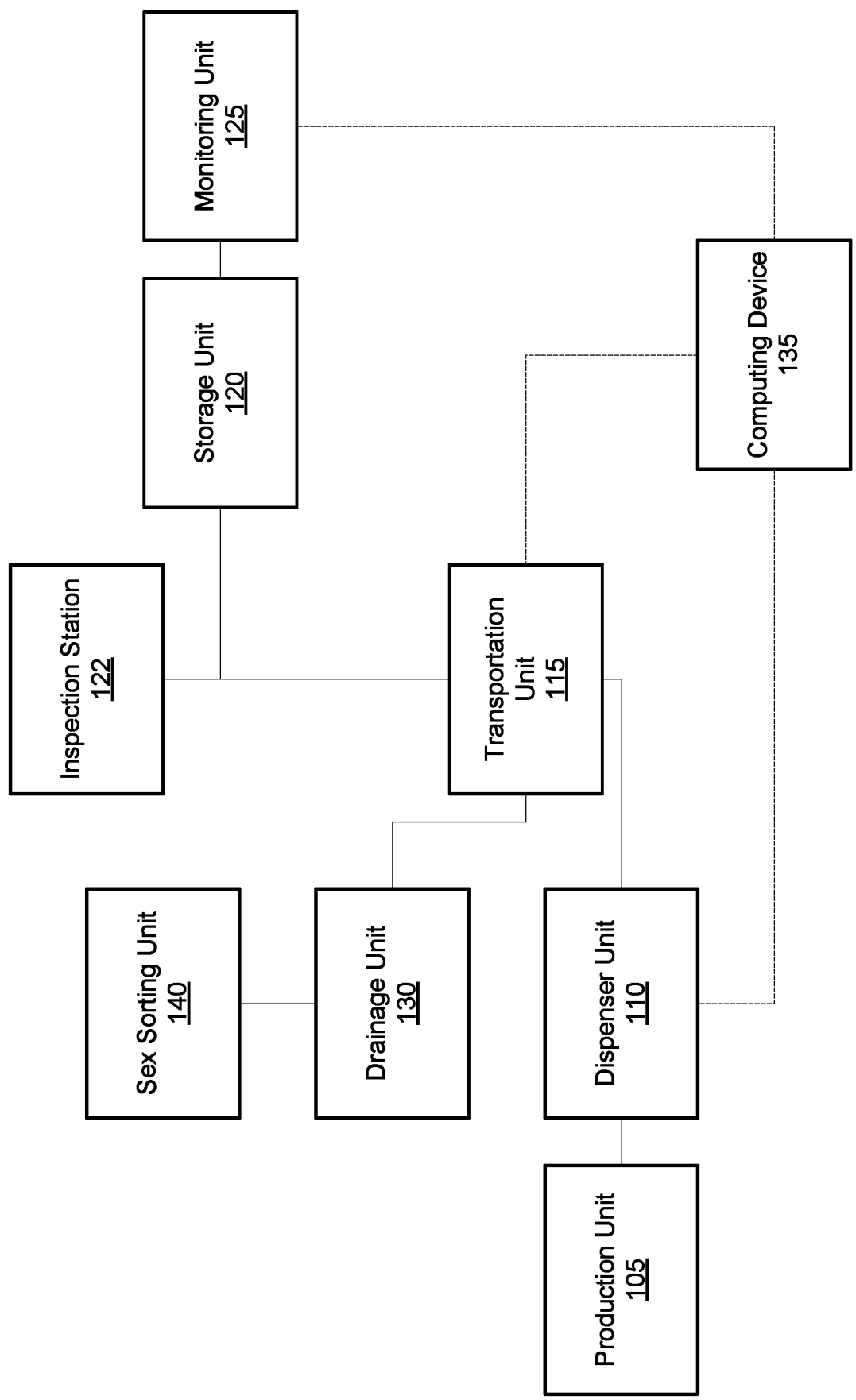
FIG. 1 illustrates a simplified block diagram of an automated mass rearing system in accordance with some embodiments.

Examples are described herein in the context of automated mass rearing systems for insect larvae. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Some embodiments can provide an automated mass rearing system for insect larvae. The automated mass rearing system can facilitate hatching, feeding, monitoring the growth and emergence of insect larvae and pupae. In some embodiments, the automated mass rearing system can include a production unit, a transportation unit, a storage unit, a dispensing unit, and a monitoring unit. In some embodiments, this automated mass rearing system can facilitate mass mosquito growth from egg hatching all the way through to full adults or certain stages in between such as the larvae rearing process (i.e., from larvae to pupae) with little or no human intervention. By automating the rearing and transportation of insect eggs, larvae, and pupae, deaths or developmental issues can be minimized. Various techniques and apparatuses are used in this automation that causes minimal disturbance to the insects while they're developing, and thereby maximizing survival rate and fitness of the insects.

Certain embodiments can automatically create of one or more insect rearing containers for housing insect eggs, larvae, or pupae. An automated mass rearing system can roll out a thin film of pliable material (e.g., pliable plastic) that would form the bottom layer of a container. Some embodiments may create form for the container by inserting one or more indentations on at least one side of the container. For example, one or more posts can be formed on the bottom layer of the container to keep a top layer from sagging down onto the contents in the container. In some embodiments, the posts may also permit an air gap to form between the solution in the container and the top layer of the container as the container is filled (e.g., with water, food, larvae). A top film can then be sealed onto the bottom layer using a heat sealer to form a bag or a pouch that can contain eggs, larvae, or pupae.

After the insect rearing container is created on a surface of the automated mass rearing system, the container may be moved along an assembly line to be filled with one or more insects (e.g., insect eggs, insect larvae), water, food, etc. In some embodiments, the automated mass rearing system can automatically dispense insect larvae (or eggs), food, solution (e.g., water), or other substances (e.g., chlorine or other types of material to help keep the environment sterile) into the container using one or more dispensers. In some embodiments, eggs, larvae, food, solution, or any additives may be added to the bottom layer of the container before or after the top layer is sealed over the bottom layer. Some embodiments may keep a small opening when the top film is being sealed against the bottom layer to allow any addition of food, solution, or other materials into the container during larval rearing. Certain embodiments may seal the edges of the two layers and create a hole at the top layer of the container by cutting off an edge of the layer or by poking a hole using a sharp tool.

Throughout the rearing process, the automated mass rearing system may automatically dispense food into the container on a periodic basis (e.g., preconfigured by a lab technician). In some embodiments, the automated mass rearing system may automatically dispense food into the container responsive to determining that there is a need to add food to any particular container, such as upon detecting that the food is running low in any particular container (e.g., using a sensor that can distinguish between food and larvae in the rearing container and comparing the amount of food against a threshold amount), upon detecting that the size of the insect larvae is smaller than usual, upon detecting that the food is not being consumed by the insect larvae, etc. Certain embodiments may also determine the type of food, its content mixture, and its consistency (e.g., sludge, capsule, etc.) depending on the status of the insect larvae (e.g., its reaction to other types of food or consistency) monitored by one or more sensors of the automated mass rearing system.

Some embodiments facilitate the automatic transportation and storage of the one or more containers for housing insect eggs, larvae, or pupae. After the insect rearing container is filled, the container may be moved along the assembly line to a portion of the surface where the container may be automatically moved, by one or more robotic arms of the automatic mass rearing system, to a storage area that is part of or coupled to the automated mass rearing system. The automated mass rearing system can have one or more robotic arms that can transport individual containers or trays on which the containers may sit.

In some embodiments, the one or more robotic arms can have one or more gripper arms that have one or more vacuum cups or suction cups that can pick up the container by its top layer using a vacuum seal. In some embodiments, there may be four or six suction cups distributed across the top layer when the suction cups are pressed against the top layer of the container. By having the container picked up from multiple points across the top layer, the force applied across the top layer of the container would be fairly even. This enables the sagging at any portions at the bottom of the container to be fairly even such that there are not any particular portions sagging more than other portions. Movement or disturbance of particles and eggs, larvae, or pupae inside the container may also be reduced.

In some embodiments, prior to storing the one or more containers in a storage area, the container may be placed on a flat tray. In certain embodiments, the tray may have designated areas for one or more containers on each tray. One or more robotic arms of the storage and retrieval unit can automatically move the tray with the container placed on the tray into a storage shelf. The storage area may include many storage shelves that will allow the trays to be stacked against one another in a space-efficient manner. As a robotic arm brings one tray into the storage area, it may retrieve another tray and bring it out of the storage area. In some instances, the tray that is being brought out can be placed on the drain station, where the contents of the disposable container can be drained into a gutter that then collects the pupae in an emergence pipe. The disposable containers can then be disposed into a waste bin.

Some embodiments can automatically monitor the growth of the eggs, larvae, and pupae using one or more sensors and automatically adjust parameters surrounding the growth of the eggs, larvae, and pupae. After the containers are placed into storage for a set period of time and at set intervals, the containers may be inspected. In some embodiments, the containers are inspected by the one or more sensors at the storage area or at a surface of the automated mass rearing system to which the containers are transported (e.g., by one or more robotic arms). In certain embodiments, the containers may be inspected at an inspection station of the automated mass rearing system. A container may be transported to the inspection station via one or more robotic arms. The automated mass rearing system may collect data on rearing containers via one or more sensors at the inspection station.

In some embodiments, in addition to monitoring the growth of the insects, the automated mass rearing system may monitor the storage area and the rearing container environment. For example, the automated mass rearing system may monitor the temperature and lighting of the storage area and the rearing container environment via one or more sensors. The automated mass rearing system may include one or more temperature and lighting controls for adjusting those parameters in the storage area, such as the temperature or the lighting surrounding one or more rearing containers. Some embodiments may automatically adjust those parameters based on preset goals and thresholds, or based on the development of the insects. For example, some embodiments may determine that the larvae is developing at a slow pace and thereby increase the temperature and lighting.

The automatic monitoring reduces the need for manual inspections and adjustments based on the inspection results, thereby drastically reducing any human labor that would be involved otherwise. Further, the automation of these processes enables consistent processing on the insects (e.g., mosquitos) that are being reared by this automated rearing system. The parameters for the conditions of the containers can be fine-tuned and adjusted in a precise manner. This would enable the results to be highly efficient, accurate, and predictable.

Further, the automated food and water dispensers may automatically dispense additional food or water into the containers throughout the automated rearing process. In some embodiments, the amount of food, water, or other additives dispensed may depend on the development of the larvae. Some embodiments may dispense more food than the standard amount upon detecting that the larvae or under-developing, for example. The frequency of the dispensing may also vary depending on the development of the larvae. For example, the automated mass rearing system may automatically increase the frequency at which the food is dispensed by the food dispenser upon detecting that the larvae is developing at a slower pace and at a smaller size. The water environment in the rearing containers may also be changed automatically by the rearing system by draining the water at a surface of a draining station (e.g., via a water pump and a filter), refilling the water (e.g., via a water dispenser) and adding air (e.g., via an air pump), etc.

After the mosquitos in a container are ready for emergence (e.g., mosquito larvae has evolved into pupae), the automated mass rearing system may transport the container to a drain station that is part of the rearing system. In some embodiments, the change in the state of the insect may be detected by one or more sensors. In some embodiments, the drain station may include a surface, a blade, and an emergence vessel (e.g., tube). The contents of the rearing container can be drained into an emergence vessel. After the container is transported from the storage area to the drain station via one or more robotic arms, the automated rearing system may cut open the container using a blade and allow the contents to be dispensed into the emergence vessel to move the pupae into a further container to mature into adult insects.

FIG. 1 illustrates a simplified block diagram of an automated mass rearing system 100 in accordance with some embodiments. As shown in FIG. 1, automated mass rearing system 100 can include machinery that can include multiple components, including a production unit 105, a dispenser unit 110, a transportation unit 115, a storage unit 120, an inspection station 122, a monitoring unit 125, a drainage unit 130, a computing device 135, and a sex sorting unit 140. The computing device 135 is in communication with one or more of the various units or stations to control their operation to fill rearing containers with larvae, food and other material, and to rear the insect larvae within the containers until they have matured into adult insects. As may be seen in FIG. 1, the computing device 135 is in communication with the dispenser unit 110, transportation unit 115, and monitoring unit 125 to control their respective operation. However, in other examples, the computing device 135 may also be in communication with other or different units, including the drainage unit 130 and sex sorting unit 140. Further, in some examples, there may be more or fewer components to automated mass rearing system 100 than those shown in FIG. 1.

To provide for the automated mass rearing of the larvae, the system 100 receives newly-created disposable rearing containers, fills them with larvae, food, and water (and other materials, in some examples), transports them to a storage facility, where the system 100 monitors the development of the larvae in the rearing containers, adding food, water, and air as needed based on the detected development of the larvae, and ultimately releases the larvae from the rearing containers into an environment for adult mosquitoes.

As a part of the mass-rearing process, the system 100 may first create the disposable rearing containers. In some embodiments, production unit 105 can create one or more disposable rearing containers (also referred to as rearing bags or rearing pouches throughout this disclosure) for housing insect eggs, larvae, or pupae. In various embodiments, production unit 105 can include a mechanical device such as a disposable container fabrication machine or a multi-vac machine that can fabricate disposable rearing containers. In certain embodiments, the mechanical device can be equipped with one or more rolls of heat moldable material (e.g., plastic). The one or more rolls of heat moldable material can be unrolled and laid out to form the rearing container. Some embodiments may lay out two layers (or two cut sheets of the heat moldable material) to form top and bottom layers of the rearing container. Certain embodiments may lay out a single layer to form the entire container. Different embodiments may form the container using the rolls of material differently. Further, some embodiments may include a heater that heats the edges of a layer such as the bottom layer to create a curvature at the edges. The curvature at the edges enable the bottom layer to contain substances such as water.

The production unit 105 can be further equipped to form one or more protrusions (also referred to as posts) on one or more layers of the heat moldable material. The production unit 105 can have a heater that heats the heat moldable material as it passes the heater in an assembly line. The production unit 105 may also have a stamping device or an air blowing device that causes the shape of the protrusion to form when either stamped against the heated material or when the air is blown against the heater material, respectively. Some embodiments may further include a cooling device that allows the shape of the protrusion to firm. The production unit 105 can be a part of and built into larger machinery that automates the entire process for mass larvae rearing in some embodiments.

In certain embodiments, the disposable rearing container can be made of a disposable, pliable material, such as thermoplastic. Thermoplastic is a plastic material that can be moldable when heated above a certain temperature and solidifies when cooled. By using a disposable material that is low cost and thereby cost-effective to use only once for an entire rearing lifecycle, automated mass rearing system 100 would not require any cleaning of reusable tubes or other rearing containers. As the disposable container are single-use containers and not reused for another rearing lifecycle, contamination may be reduced. Each time the rearing containers are dispensed for a new production, the rearing containers are clean. Conventional methods of using reusable bins or trays requires cleaning after each production cycle and is labor intensive in that manner. However, certain embodiments can use reusable rearing tubes or other types of containers if desired.

In some embodiments, the rearing container can be completely closed, completely open, or partially open. Certain embodiments include a sealing machine (e.g., a heat sealer) that seals a top layer of the moldable material to the bottom layer of the material to form a container. In some embodiments, the sealing machine may have one or more heaters that heats the edges of the sheets to cause the edges to fuse together. In certain embodiments, the container can be nearly sealed but with a small hole in the top film that can be gas permeable. In some embodiments, the small hole permits an exchange of oxygen. Certain embodiments may create larger openings to permit larger air exchange. Keeping the pouches nearly sealed also keeps the smells emitted by the larvae contained.

After the rearing container has been created, the system 100 moves the container to a dispensing unit 110, which fills the container with insect larvae and additional material used to rear the larvae. For example, the system 100 may move the rearing container along a conveyor or using a robotic arm. Once the rearing container has arrived at the dispensing unit 110, the dispensing unit 110 dispenses material into the rearing container.

In some embodiments, dispensing unit 110 may include one or more containers with quantities of various materials, such as larvae, foodstuffs, water, etc. Each of these containers may have a dispensing tube running from the container into a dispensing area of the dispensing unit 110. In addition, the dispensing unit 110 is in communication with a computing device 135, such as the example computing device 500 shown in FIG. 5, which controls the amount of each material dispensed into each rearing container. For example, the computing device 135 may be programmed with pre-defined quantities, e.g., weights or volumes, of larvae, food, water, etc. Upon receiving a signal from the dispensing unit 110 that a new rearing container has arrived, the computing device 135 may activate one or more valves in a pre-defined sequence (or simultaneously) to dispense material into the rearing container.

For example, the dispensing unit 110 may employ the tubes to dispense water, insect eggs or larvae, food, and any other additive desired by the lab specialist into the rearing container. In various embodiments, dispenser unit 110 can further include one or more vats or containers of food slurry or liquids (e.g., water or other type of solution) or other additives, and one or more valves that can be opened to dispense food, liquids, or other additives, or shut to stop the dispensing. The one or more tubes can dispense the food, liquids, or other additives from the food container, liquid container, or other additives container into an opening of a rearing container. The valves in this example are electromechanical, i.e., they can be opened or closed by electrical signals or commands. The rate at which the water, food, and any other additives are dispensed through the tubes may be specified and adjusted e.g., by the valves.

Further, dispenser unit 110 may also include a grinder or a mixer that can grind up different food ingredients and mix the different ingredients into the food based on a configuration specified by an administrator of the automated mass rearing system. The parameters for the food slurry or the liquid solution can be predefined in the computing device 135 and the grinder or the mixer may be activated after a new rearing container has arrived at the dispensing unit.

In some embodiments, dispenser unit 110 may dispense food into the rearing container one or more times during a rearing process of the mosquitos, after the initial stage during which the rearing container is created and the eggs or larvae, water, and food are added. For example, the rearing process may take an extended period of time during which the larvae may consume most or all of the food or air within the rearing container, or fresh water may be needed periodically through the rearing process. Thus, the system 100 may periodically return a rearing container to the dispensing unit 110 based on a pre-defined schedule, or based on a detected low level of food or water, or poor air or water quality. The process for returning a rearing container to the dispensing unit is described in more detail below. However, after receiving such a rearing container, the dispensing unit may again dispense the needed material into the rearing container. As discussed above, the computing device 135 may be programmed with one or more parameters related to an initial mix of materials to be dispensed into a new rearing container. For re-filling the rearing containers, the computing device 135 may determine a quantity of food, water, air, etc. based on sensor signals obtained from a monitoring unit 125 discussed below. Alternatively, the computing device 135 may instead use a preset quantity to refill the rearing container with the needed material.

In certain embodiments, dispenser unit 110 may also include an egg dispenser or a larvae dispenser that can dispense eggs or larvae. Dispenser unit 110 can include an egg container that can include one or more eggs or a larvae container that can include one or more larvae. Dispenser unit 110 can further include a tube or a vessel that can dispense the eggs or the larvae from the egg container or the larvae container into an opening of a rearing container. One or more valves can control the rate at which the eggs or larvae are dispensed and when they are dispensed.

In some embodiments, dispenser unit 110 may have other means of dispensing the insect eggs or larvae. For example, dispenser unit 110 may have an insect eggs container or insect larvae container and a scale that can weigh and measure an amount of eggs or larvae to be transported through a tube to the container. The insect eggs or larvae may be automatically counted (e.g., based on total weight) and dispensed into each disposable container when the container (or at least the bottom layer of the container) has been created.

The system 100 further includes a transportation unit 115 that is employed by the system 100 to transport rearing containers between various components of the system. The transportation unit 115, as will be described in more detail below, may include one or more articulating robotic arms, one or more conveyor belts, etc., to transport individual rearing containers, or one or more trays holding one or more rearing containers. The transportation unit 115 may transport filled rearing containers from the dispenser unit 110 to a storage unit 120, or from a storage unit 120 to a drainage unit 130, an inspection station 122, or back to the dispensing unit 110. In some embodiments, one or more articulated arms can be connected to a base and have one or more forks (also known as blades or tines) on the other end of the arm(s). The blade can be used to lift objects such as a tray or even a container. In some embodiments, the robotic arm can move across the different aisles of the storage area. In certain embodiments, the base of the robotic arm can be connected to another machine or movable platform that can transport the base across the different isles of the storage area. The base or the movable device to which the base is connected can be connected to the automated insect rearing system.

In certain embodiments, transportation unit 115 can transport the rearing containers that contain insect eggs or larvae onto a storage rack. In some embodiments, transportation unit 115 can include one or more robotic arms that can move in one or more degrees of freedom ("DOF"). In certain embodiments, transportation unit 115 can include a multi-DOF robotic arm (e.g., articulated-arm robots). In some embodiments, one or more articulated arms can be connected to a base and have one or more suction cups on the other end of the arm(s). The base can be connected to the automated insect rearing system. Certain embodiments may have arms that are able to transport objects using other means, such as magnets, electromagnets, adhesives, etc. In some embodiments, the rearing containers that are being transported also includes water and food for the insects. Transportation unit 115 can be configured to transport the rearing container swiftly and accurately to minimize the disturbance of the contents in the rearing container.

In some embodiments, based on commands received from the computing device 135, a robotic arm of transportation unit 115 can pick up a rearing container by suctioning the top of the container using one or more suction cups. Transportation unit 115 can minimize disturbance to the water by moving the containers in a controlled fashion. In some embodiments, the robotic arm may accelerate and decelerate slowly so that there are minimal ripples created by the liquid content. The more the larvae are disturbed, the smaller the mosquitos may turn out and the more likely they will not be viable. By automating the transportation of the rearing containers, the movement of the bag and the disturbance to the larvae are minimized, thereby allowing a larger percentage of the larvae to survive and a smaller percentage to be stunted in its development.

After picking up the rearing container, the robotic arm of transportation unit 115 may then move the container into a carrier tray. In certain embodiments, the carrier tray can hold more than one rearing container. In some embodiments, the robotic arm of transportation unit 115 can also serve to transport the rearing container(s) into a storage area.

In some embodiments, transportation unit 115 can then transport the carrier trays to a storage unit 120. In this example, the storage unit 120 has multiple storage racks having one or more storage shelves. Each storage rack can then each store one or more carrier trays in each of its storage shelves.

In some examples, the storage unit 120 may include one or more environmental controls to adjust the storage environment for the rearing containers. For example, the storage racks of the storage unit 120 may each be enclosed with vents to receive warm or cool air from a heating or air conditioning system. In some examples, the environment of each storage rack may be individually adjusted by opening or closing one or more vents. However, in some examples, the various storage racks may be stored in a common area, e.g., a room, with a common environment. Temperature controls, such as a thermostat, may be used by the computing device 135 to adjust a heating or cooling system based on a sensed temperature within an individual storage rack or within the storage unit itself. For example, the computing device may receive sensor signals from the monitoring unit 125, detect an environmental condition associated with the rearing container, and in response to determining the environmental condition exceeds a predetermined setting, modify an environmental control based on the environmental condition and the predetermined setting, such as to change a temperature, humidity, or lighting condition within the storage unit 120.

In addition to temperature controls, the storage unit may also include other types of controls, such as lighting controls or humidity controls. For example, lighting within an individual storage rack, or within the storage unit 120 itself, may be adjusted by turning lights on or off, or by adjusting a level of dimming on one or more lights. Similarly, a humidity level within the storage unit (or individual storage racks) may be adjusted by the computing device 135 based on preset desired humidity levels and sensed humidity levels received from the monitoring unit 125.

Once the rearing containers have been moved into the storage unit 120, they are monitored by one or more sensors from the monitoring unit 125. For example, the monitoring unit 125 may employ temperature sensors, humidity sensors, light sensors, cameras, pressure sensors or scales, etc. to monitor the individual rearing containers or the environment of the storage unit 120 itself. For example, in certain embodiments, monitoring unit 125 can monitor the environment in which the rearing containers are located and the contents of the rearing containers. In some embodiments, monitoring unit 125 may be in communication with the computing device 135 and provide information from one or more sensors to the computing device 135. The computing device 135 may then adjust one or more settings within the storage unit, or may command the transportation unit 115 to retrieve one or more rearing containers for further action. For example, the computing device 135 can receive sensor information, determine an amount of food in the rearing container based on the sensor information, determine, based on the amount of food and a predetermined threshold amount of food, whether to transport the rearing container from the storage unit 120 to the dispensing unit 110 to dispense more food, water, air, etc. into the rearing container, and then return the rearing container to the storage unit 120.

In some examples, the mass rearing system 100 may include a manual inspection station 122 to allow one or more users to visually inspect one or more rearing containers. In this example, a user may select one or more rearing containers using the computing device 135. For example, the user may review sensor information about rearing containers within the storage unit 120 and select one or more for manual inspection. After the user has selected the desired rearing containers, the computing device 135 transmits one or more signals to the transportation unit 115, which retrieves the selected rearing containers from the storage unit 120 and transports them to the inspection station 122. In this example, the inspection station is made up of one or more tables or other flat surfaces. The user may then inspect the rearing containers and, if needed, specify particular actions to be taken using the computing device 135. For example, the user may simply return one or more of the rearing containers to the storage unit 120, or she may indicate that additional food or water (or another material) is to be added to the rearing container, or that the rearing container should be opened and drained to obtain matured insects. In response to such commands, the computing device 135 may then transmit one or more signals to the transportation unit 115 to transport the rearing containers to the appropriate stations for further action.

In some embodiments, the computing device 135 can monitor the development of the mosquito larvae in the rearing container using information detected from one or more sensors (e.g., a camera). The computing device 135 can determine how much food there is remaining in the rearing container based on images captured by an imaging sensor. Based on the amount of remaining feed in the rearing container, dispenser unit 110 may automatically dispense more or less food.

In certain embodiments, the sensor may be an infrared sensor (or other spectral imaging sensor) that can be used to monitor the amount of remaining food in the bag. The infrared sensing can also help distinguish different content within the rearing container, such as food from larvae, as some of the different objects within the rearing container may not be easily distinguished from each other just via the naked eye.

In some embodiments, the sensor(s) can help the computing device 135 monitor the health of the larvae. The computing device 135 can receive sensor signals from one or more sensors and calculate, based on data received from the one or more sensors, the number of live larvae, the size of the larvae, in addition to determining how much food is remaining in a container (also referred to as a tray) at any particular moment. Some embodiments may also measure the quality of the water, which may be another factor taken into account in determining the health of the larvae.

In some embodiments, the computing device 135 may maintain various parameters and other information related to the mass rearing system 100 or the types of insects being reared within the system. For example, the computing device 135 can store media items such as audio files, video files, or image files; information about the different types of insect or mosquito species; parameters set for each of the rearing containers, monitored results from various sensors for each of the rearing containers, conditions configured for each of the rearing containers (e.g., adjusting a parameter of the rearing container when certain criteria are met).

In certain embodiments, the computing device 135 can store process parameters of one or more rearing containers. Examples of process parameters can include the number of live larvae at certain stages of development, the size of the larvae, the amount of food being fed and the intervals at which the larvae are being fed, the frequency at which the larvae are being fed, the temperature under which the larvae are being placed, the amount of water and the water depth in which the larvae are being placed, rules specifying to trigger an alert or to display on a user interface responsive to certain conditions of the rearing container or larvae exceeding a threshold, etc. In some embodiments, the rearing containers may be tagged to enable the automated rearing system to track the different rearing containers.

In some examples, the computing device 135 can process data (e.g., sensor signals from one or more sensors) received from one or more stations within the mass rearing system 100 and perform calculations based on the data and perform one or more actions responsive to the calculation. For example the computing device 135 can calculate an amount of food to dispense to a rearing container when replenishing the food supply for the larvae in the rearing container and cause dispenser unit 110 to dispense the calculated amount. Computing device 135 can also cause information (e.g., an alert) to be displayed on a user interface based on the data.

In some embodiments, the computing device 135 may display a user interface and can include one or more input and output devices. A user can operate input devices to invoke the functionality of system 100 and can view, hear, or otherwise experience output from system 100 via output devices of user interface 140. In some embodiments, an administrator of the automated rearing system 100 or a lab technician can input specific configurations or adjustments for the rearing of the insect (e.g., amount of food, water, air dispensed into a container, adjustments that are to be made in response to data obtained through one or more sensors, etc.) via the user interface.

Some embodiments enable the administrator to customize each rearing container to contain different amounts of content and to be placed under a set of conditions (e.g., specified by one or more process parameters). In certain embodiments, a user interface may also display information pertaining to any particular rearing container. Examples of information that may be displayed via the user interface include data obtained through a sensor, one or more process parameters of a rearing container, changes in a rearing container, any alerts upon detecting and determining that one or more parameters have exceeded a predetermined threshold, etc. Further, the computing device 135 may enable a user to control the robotic arms, e.g., using a mouse to select one or more rearing containers and a destination for the rearing containers, or by manually controlling one or more robotic arms.

In some embodiments, a rearing container may be drained of waste, water, air, or other material during the course of rearing insect larvae. For example, the computing device 135 may determine a low food condition or a poor water quality condition of the rearing container via many different ways, such as based on scheduling software or sensor signals received from the monitoring unit 125. The computing device 135 may then command the transportation unit 115 to retrieve the rearing container from the storage unit 120 and transport it to the drainage unit 130. The drainage unit 130 can drain the contents of the rearing container. For example, the contents may be drained and the larvae collected using a filter. The larvae may then be transported to a new rearing container. In some examples, however, the drainage unit may unseal a portion of the rearing container and selectively drain water or other material from the rearing container, while leaving the larvae in place within the rearing container. In some instances, the contents of the rearing container can be drained on the rack directly, instead of having to move the rearing container to the drainage unit 130. A small incision may be made on the rearing container to allow the contents to be drained from the rearing container.

If the computing device 135 determines that the larvae are maturing into adult insects, the computing device 135 may command the drainage unit to drain the larvae into an emergence pipe. In one such example, the drainage unit 130 can include a surface plate, a blade, a gutter, a funnel, and an emergence pipe. The surface plate may be where the bag may be placed after storage unit 120 retrieves the tray from the storage rack and transportation unit 115 moves the bag from the tray. The blade then can then cut the bag open while it is set on an angle on the surface plate. The contents of the bag may be poured into the gutter. The funnel may then help direct all the contents including the pupae into the emergence pipe. The pupae may then emerge into adults in the emergence pipe.

Further, in some embodiments, system 100 can include an automated sex sorting unit 140 that includes an imaging device and an ultrasound for sorting adult insects that have matured from the larvae within the rearing container, or even before the larvae have matured into adults. For example, pupae can be sorted by various features that may distinguish male from female such as size, weight, etc. Some embodiments can sort the male from the female in one or more stages. Certain embodiments may sort the sex using a two stage approach. Before the pupae emerge into adults, some embodiments may use an imaging device to determine the size of the pupae in the emergence pipe and sort the pupae based on the sizes. Some embodiments may further sort the sex after the pupae emerge into adults to increase the accuracy of the identified gender of the insects. In some embodiments, ultrasound (e.g., Doppler ultrasound) can be used to detect a wingbeat frequency of the adult insect. By determining the wingbeat frequency of the adults, sex sorting unit 140 can identify the male insects from the female insects. Some embodiments may further distinguish the various species of the insects from each other based on features and properties of each species.

In some embodiments, a Doppler system for determining a characteristic of an insect can comprise a control unit that can include a sensor. The sensor can transmit and receive signals. The signals may be sound, light (e.g. laser), or radar signals. The signals may be ultrasonic signals. The sensor can include a separate transmitter and a receiver for emitting and receiving the signals. In some examples a combined transmitter and receiver (i.e., a transceiver) may be used. The transceiver can be a positioned near an opening to a vessel or container, such as a tube, within the container, or in some examples outside the container with a view into the container. An insect may fly through the container and past the transceiver. The transceiver can emit a signal, for example a sound wave, having a particular frequency. The signal emitted by the transceiver can reflect off the moving wings of the insect and off the insect's body as it flies through the container and past the transceiver. The transceiver can receive the signal reflected off the wings and body of the insect.

The reflected signal may have a frequency that is different from the frequency of the signal emitted by the transceiver. The difference between the signals, for example the change in frequency of the signal can be used to determine the speed of the insect. The change in the frequency of the signal can also be used to determine the wing beat frequency of the insect. The wing beat frequency is the number of complete wing beats per second, in other words the number of complete cycles of wing movement per second. One example of a complete cycle of an insect's wing movement can be the wings moving from a highest point, downward to a lowest point, then upward back to the highest point.

Figure 2:
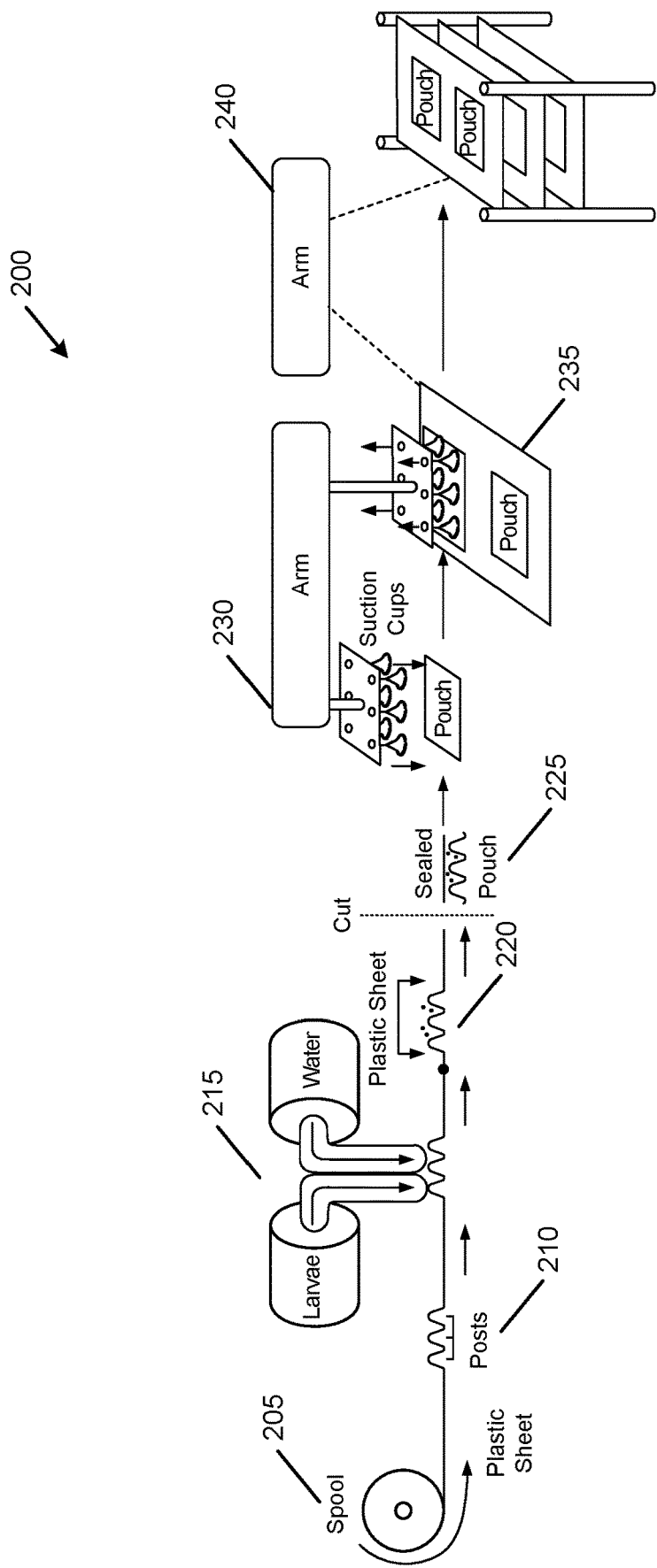
FIG. 2 illustrates a simplified automated process of mass rearing insect larvae performed by an automated mass rearing system in accordance with some embodiments.

FIG. 2 illustrates a simplified automated process 200 of mass rearing insect larvae performed by an automated mass rearing system in accordance with some embodiments. In some instances, one cycle of this rearing process can take about five days to a week for some insects such as mosquitos.

Some embodiments can have one or more spools of plastic or other pliable material that can be used to form a vessel such as a bag, tray, or tube for harvesting the insect larvae. Some embodiments may create the one or more disposable rearing containers by rolling out a layer of the disposable material from a roll of the material onto a flat surface. In certain embodiments, the film is made of a pliable plastic material. In different embodiments, different material can be used to create the rearing containers.

As shown at 205, a layer of plastic material can be laid out from the spool of plastic. In an example, there can be two rolls of plastic material where a layer or thin film from the bottom roll can be brought up and heated from underneath the platform to form a shape as the bottom half of the bag.

At 210, one or more posts can be automatically formed into the bottom layer for the tray. In certain embodiments, one or more posts or protrusions can be formed throughout the bottom layer for support. Having the posts on the bottom layer may prevent the top layer from collapsing onto the water (or solution) injected into the pouch when the top layer is laid against the bottom layer for sealing. In addition to providing support, the one or more posts can keep the top upright, thereby maintaining a particular orientation for the pouch.

Certain embodiments may automatically inject the insect larvae and water (and, in some examples, food or other additives) into the bottom layer before sealing the pouch with the top layer. As shown at 215, larvae and water are dispensed into the bottom layer of the container. Certain embodiments may add chlorine or other types of additives to keep the contents sterile.

At 220, a pouch may be formed by applying a top layer from the same roll (or a different roll) onto the bottom layer. An enclosed or nearly enclosed pouch can be formed when the two films are placed against one another and sealed at the edges or more connecting points throughout the pouch, such as that shown at 225. In certain embodiments, the vessel may be open, sealed, or have a removable lid. In some embodiments, the bag may not be completely closed but partially or nearly sealed, which create a good barrier to the environment. The nearly sealed environment for larval rearing can keep out mold and bacterial and maintain consistency from bag to bag. The chances of cross contamination or spreading a potential infection from one bag to another would be minimal. Further, an air space can be kept in the bag to allow mosquito larvae to breath from the air space. By creating an air pocket, the larvae can have a higher chance at staying viable.

A transportation unit can handle transfers from a production unit to a storage and retrieval unit. The storage and retrieval unit can take all the bags and store them in individual storage areas. The storage areas can be temperature controlled to enable the insect larvae to grow quickly. The storage and retrieval unit may also handle additional feeding cycles throughout the rearing process.

The automation enables gentle movement when transporting the trays and minimizes collisions between objects in the bag and against the surfaces of the bag. This increases the chances of mosquito survival greatly as opposed to a human manually carrying and transporting trays. As shown at 230, a robotic arm can use suction against the top surface of the pouch to handle and transport the pouch. In this example, there are 6 suctions distributed across the width and length of the pouch so that there would be minimal sagging of any portions of the bag when the bag is lifted. The process has been designed to minimize disturbance to the contents of the bag.

At 235, the robotic arm can place the bag onto a tray that can hold multiple bags. At 240, another robotic arm may lift the tray and transport the tray to a storage rack in a storage area. The storage area may include a large number of storage shelves that are lined up in many rows. In certain embodiments, the robotic arm may travel along a track in the storage area to arrive at a particular set of shelves before articulating to place the tray on a particular shelf In some embodiments, the racks may be stacked on top of each other so that the space may be used effectively.

In some embodiments, the storage and retrieval system enables the rearing larvae to have a controlled environment. For example, the temperature may be kept at very even levels throughout the whole incubation period so that the entire process is carefully controlled. By keeping the process controlled and consistent, the larvae may grow at a similar rate and thereby ensure consistency throughout.

When the insect larvae are ready to emerge (e.g., turn from pupae to adult mosquitos), the transportation unit can transport the bag to a drain station. In some embodiments, the drain station may not be a part of the automated rearing system in a manufacturing location and can be outside the factory. In certain embodiments, the transportation unit places the bag on the drain station, slits the bag, and drains the pupae into a pipe where the pupae may emerge into adult insects.

In some embodiments, the automated rearing system also includes a sex separation unit where the female mosquitos may be sorted from the male mosquitos. After the mosquitos are sorted, a release container process then releases the sorted males into the wild. This automated larvae rearing system requires very little human input and saves a tremendous amount of labor compared to other insect rearing systems.

Some embodiments enable the configuration and implementation of numerous different rearing programs simultaneously. The automated larvae rearing system may keep track of each individual program, its parameters and conditions, and its outcome. By having the ability to keep track of these different programs, many parameters may be optimized, including cycle time, the growth, density, etc. by changing different variables such as the diet, the temperature, etc. This automated system allows a scientist to alter just one variable at a time while keeping all the other parameters controlled. To have a scientist carry out these various optimization procedures and explore each parameter would be extremely labor intensive. The automated system may also have altered feeding cycles for different containers such that some may have a quicker feeding cycle while others may have a slower feeding cycle. Without this automated system, it would be difficult to keep track of the different conditions under which each container out of thousands of containers is exposed.

Figure 3:
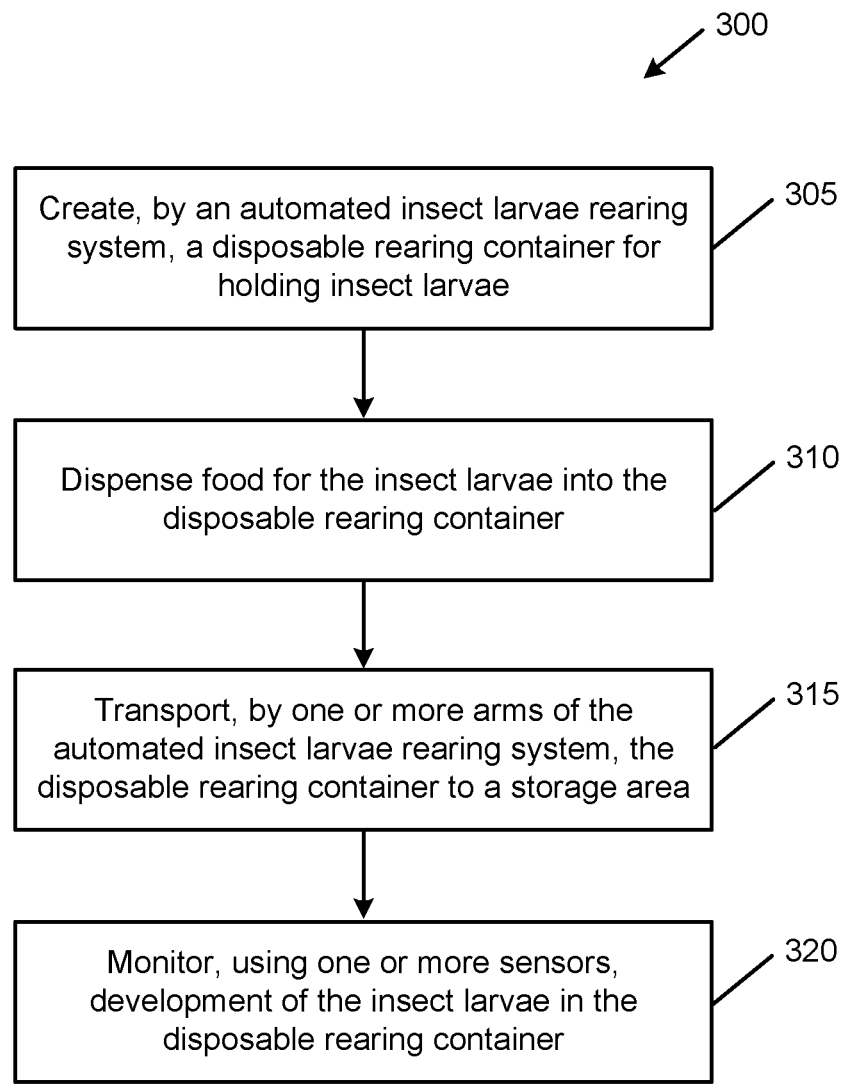
FIG. 3 depicts a flow chart for mass rearing insect larvae using an automated mass rearing system in accordance with certain embodiments.

FIG. 3 depicts a flow chart 300 for mass rearing insect larvae using an automated mass rearing system in accordance with certain embodiments. Flow chart 300 can be performed by one or more components of automated rearing system 100. These components implementing flow chart 300 may reside on an electronic device. In some embodiments, a portion of flow chart 300 may be executed by one or more processors of the electronic device.

At block 305, a disposable rearing container for housing insect larvae can be created by an automated insect larvae rearing system. As described, the automated insect rearing system can create a disposable rearing container or pouch by forming one or more posts on a flexible film sheet. The one or more posts cause the flexible film sheet to protrude at certain portions of the sheet. The protrusions cause the top film to be unable to collapse fully onto the bottom film when the edges of the films are being sealed together.

At block 310, food for the insect larvae can be automatically dispensed into the disposable rearing container. In some embodiments, the amount of larvae, food, and water to be automatically dispensed into each pouch is pre-configured by a lab technician. Some embodiments dispense food into the container periodically. In certain embodiments, additional food and water may be dispensed depending on the condition of the larvae. If the larvae appear to be under-developing, some embodiments may dispense additional food to the pouch containing the under nourished larvae.

At block 315, the disposable rearing container can be transported to a storage area by one or more arms of the automated insect larvae rearing system. In some embodiments, an arm of the automated rearing system may place each pouch onto a tray. The automated rearing system may use suction force to hold onto each pouch from its top surface. There may be many portions of the top surface that are being held by the arm to ensure that the pouch is picked up with minimal distortion to its flimsy shape. After each tray is filled, another transport arm may lift up the tray and place the tray into a rack on a shelf of racks. Some embodiments barcode or tag each container or tray so that the individual containers or trays can be tracked in a database.

At block 320, the development of insect larvae in the disposable rearing container can be monitored using one or more sensors. In some embodiments, sensors including a vision system can be used to assure and maintain process parameters. Additional sensors may include a temperature sensor, water depth sensor, turbidity measuring sensor, etc. The water depth sensor provides information on whether there is the right amount of water in each container. The turbidity measuring sensor can provide information in how clear the water is. By monitoring each container using the various sensors, the automated rearing system can provide the effects of the process in real time.

Some embodiments may detect any changes that might be causing death in the container and permit additional actions to be scheduled in real time. For example, if there is a container that is experiencing increasing deaths, abnormalities in the development (e.g., slower development where the larvae are undersized or where the sizes are being developed differently in a same container), or deformities, then the automated rearing system may observe that and provide feedback to an administrator in real time.

In some embodiments, there may be periodic dispensing of food into the disposable rearing container. Some embodiments monitor the larvae and dispense food as needed. In some embodiments, during feedings, the automated arm may pull each tray out and dispense the food into the opening of each container and push the tray back in. Reaching every container is particularly difficult and inefficient (i.e., time consuming) to be done by a person since the trays may be placed in a very high area of a storage area. Further, instead of using a disposable plastic pouch for rearing larvae, some embodiments may use reusable pipes or tubes to house the larvae.

Figure 4:
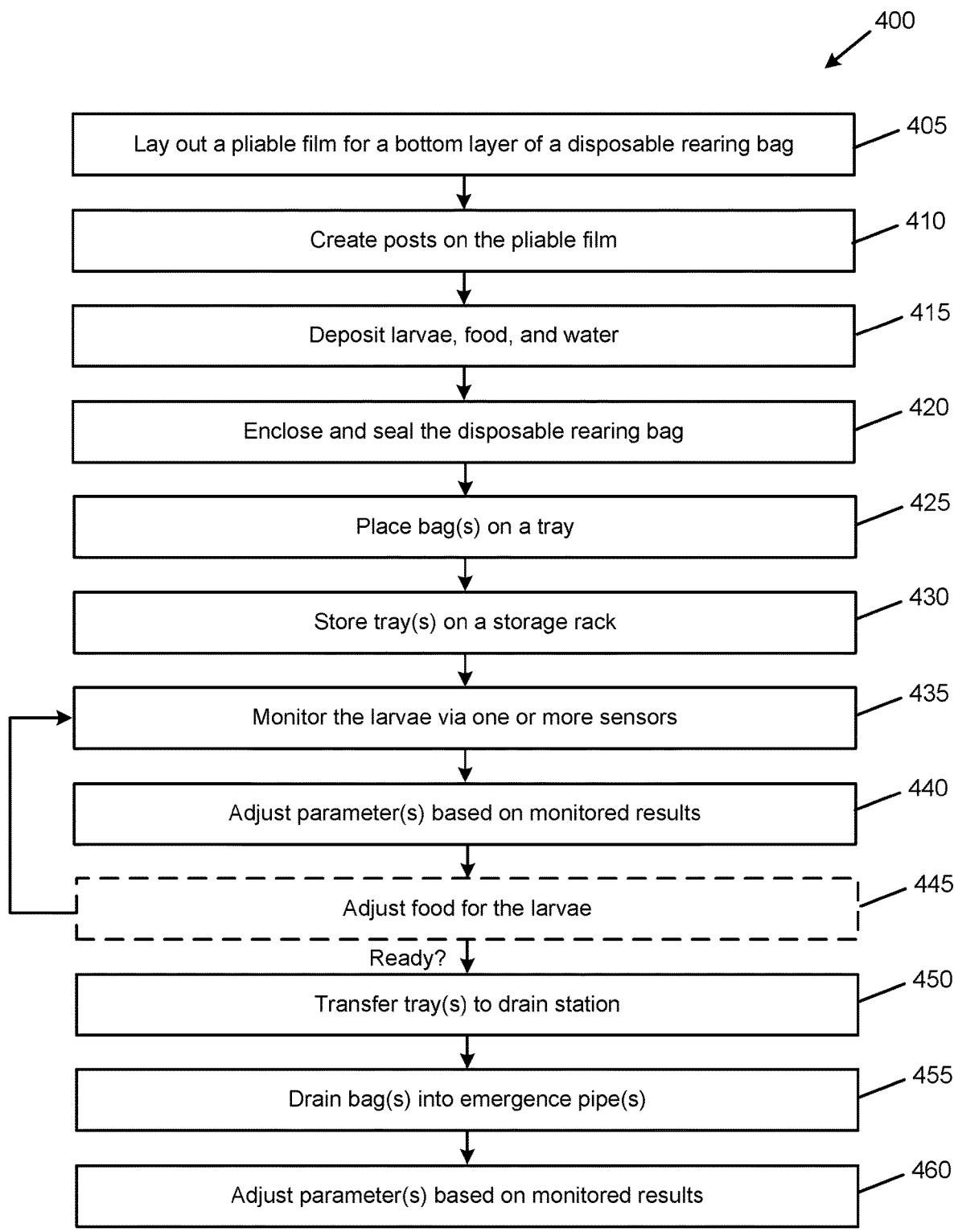
FIG. 4 depicts another flow chart for mass rearing mosquito larvae using an automated mass rearing system in accordance with certain embodiments.

FIG. 4 depicts another flow chart 400 for mass rearing mosquito larvae using an automated mass rearing system in accordance with certain embodiments. The automated mosquito larvae rearing system can include a production unit (also referred to as a multi-vac unit) that produces bags, fills the bags with mosquito larvae, food, and water.

In the creation of the containers, the production unit dispenses one or more plastic sheets to create an enclosure. The one or more plastic sheets may be sealed, or partially sealed. At block 405, the automated mass rearing system can lay out a pliable film for a bottom layer of a disposable rearing bag. At block 410, the automated mass rearing system can create posts on the pliable film. In some embodiments, the bottom layer can form one or more protrusions so that the protrusions may serve as a support structure and prevent the top of the bag from collapsing onto the water (or solution) injected (or to be injected) into the bag. In some embodiments, the protrusions may be formed by heating the plastic to make it even more flexible and blowing air at certain portions of the lower layer to get indentation(s). In certain embodiments, heat can be applied to keep the pouch sterile.

At block 415, the automated mass rearing system can deposit mosquito larvae, food, and water into the bag. In some embodiments, the mosquito larvae, food, or water are not dispensed into the bag until the top layer has been placed over the bottom layer to form a pouch, either partially sealed, fully sealed, or open. Some embodiments may then add water, food, and the larvae or eggs into the lower pouch prior to it being sealed. In some embodiments, a capsule or a nugget of time released food can be used for food dispensing. In certain embodiments, food may be dispensed periodically (e.g., semi-daily basis).

In this example, at block 420, the automated mass rearing system can enclose and seal the disposable rearing bag. In some embodiments, the disposable rearing bag need not be fully enclosed, but can be partially open.

At block 425, the automated mass rearing system may place one or more bags on a tray. At block 430, the automated mass rearing system can store one or more trays on a storage rack. In some embodiments, a transportation unit that is part of the system can transport container in which the mosquito larvae are kept until they evolve into pupae. The transportation unit can include one or more suction cups that can pick up the container from its top surface.

At 435, the automated mass rearing system can monitor the larvae via one or more sensors. In some embodiments, the one or more sensors (e.g., camera) can be placed in different zones of the storage area. The fill station can have ultrasonic sensors to determine how much water has been put into the container or how deep the water is in the container. The robotic arms may each have one or more cameras on them to look at the containers. The vision sensor can enable a lab technician to determine whether there are enough larvae, pupae, whether the water is skanky, etc.

Process parameters can be detected by one or more sensors including a vision sensor, temperature sensor, water depth sensor, turbidity measuring sensor, etc. The water depth sensor provides information on whether there is the right amount of water in each container. The turbidity measuring sensor can provide information in how clear the water is. The one or more processors can monitor and maintain process parameters based on data or sensor signals obtained from the one or more sensors. By monitoring each container using the various sensors, the automated rearing system can provide the effects of the process in real time.

At 440, the automated mass rearing system can adjust one or more parameters based on the monitored results. Some embodiments may detect any changes that might be causing death in the container and permit additional actions to be scheduled in real time. For example, if there is a container that is observing increasing deaths, abnormalities in the development (e.g., slower development where the larvae are undersized or where the sizes are being developed differently in a same container), or deformities, then the system may observe that and provide feedback to the automated system (or an administrator) in real time.

The mosquitos with developmental issues or deformities may have a harder time mating with other mosquitos in the wild and staying alive. Other factors that might also affect the fitness of the emerging mosquito are the wingbeat frequency or flight ability. The automated rearing system may record the wingbeat frequency as the mosquitos are emerging and identify those mosquitos that have a wingbeat frequency closer to the female wingbeat frequency.

At block 445, the automated mass rearing system can adjust food for the larvae. Some embodiments may program a number of recipes into the monitoring and feeding unit. In certain embodiments, the feeding can be performed on a periodic basis. In some embodiments, the feeding can be dispensed based on one or more criteria being satisfied. In certain embodiments, a monitoring and feeding unit can monitor the larvae's development in real time and control the feeding dynamically based on the feedback from the monitored development.

In certain embodiments, the automated mass rearing system may grind up food and add different ingredients based on the configuration specified by an administrator of the unit. Having the automated mass rearing system keep track of the mixture of food and liquids, and the processing of foods that are given to each container (e.g., ground, in chunks, in a slurry, in a smudge, in a pill, compressed) enables one to experiment as to the ideal feeding ingredient and schedule to maximize the output of high quality mosquitos. Additional parameters such as the temperature of the water, the amount of water in each container, the number of larvae in each container can also be applied to different containers to facilitate experimentation on the ideal output.

At 435, after adjusting one or more parameters and an amount of food for the larvae, the automated mass rearing system may continue to monitor the larvae via one or more sensors. In some embodiments, the automated mass rearing system may inspect the bags to determine whether the larvae have pupated. In some instances, further inspections on the bags may be done to ensure that the process is being maintained. When the larvae evolve into pupae, the containers are ready to be drained as the pupae get ready for emergence. During the emergence stage, some embodiments may raise the water level in the tube to push the mosquitos out of the tubes. Cleanup for the larvae rearing stage can be minimized by the use of disposable vessels or containers.

At block 450, the automated mass rearing system can transfer one or more trays to the drain station. After the pupation period (e.g., a week), the bags are brought out from the storage to the drain station. At block 455, the automated mass rearing system can drain one or more bags into an emergence pipe. The containers may be set on an angle of a plate and cut open by a blade. Once the containers are cut open, a funnel can be used to direct all the content into a vessel (e.g., a tube, a pipe) so that the pupae within the containers can be drained into the vessel. The pupae may then emerge into adults in the vessel.

Using bags as the container enables the drainage to be performed more efficiently and effectively. Instead of conventional methods of pouring one or more trays to dump out the contents, drainage using bags enable the process to be a lot more controlled. The flow rate can be better controlled and thereby enabling more pupae to survive.

Once the pupae are poured out of the containers, they can be automatically sorted by size, weight, or other distinguishing features between male and female pupae using the automated rearing system. In certain embodiments, the sorting may not be performed by the same automated rearing system but by a separate automated device coupled to the automated rearing system. In some embodiments, the females are sorted from the males by size as the females tend to be larger in size.

In some embodiments, an automatic sex sorting unit may sort the pupae before they emerge into adults. In certain embodiments, the sex sorting unit may sort the adult mosquitos. In certain embodiments, the sex sorting unit can sort the gender of the mosquitos by imaging techniques or vision systems, by wingbeat frequency, etc. Some embodiments may have an ultrasonic Doppler sensing device (e.g., an ultrasound) that can observe the wingbeat frequency. In certain embodiments, the system may sex sort the mosquitos as they fly up from the tube. As the mosquito emerges, a vision system or a wingbeat frequency measuring system can be used to sort the gender. In some embodiments, these systems may also be used to distinguish between the different species (e.g., the different thousands of mosquito species). Further, some embodiments may also use machine learning based on computer vision systems.

By having a multi-tier sex sorting system where the first tier would sort the gender at the pupae stage and the second tier would sort the gender at the full grown flying adult stage, the accuracy would be greatly increased (e.g., to an error rate at 1 in 1 million).

Certain embodiments may alter the genetics or infect these sorted male mosquitos with different bacteria or viruses using the automated system to produce large quantities of consistent and sterile male mosquitos with high fitness and mating success. In some embodiments, males produced from the automated larvae rearing system may be infected with a symbiotic bacteria such as *Wolbachia*. By mating males with the *Wolbachia* strain with wild females that have a different strain of *Wolbachia* or no *Wolbachia* at all, the females will produce eggs that are not viable. Some embodiments may utilize RNA interference to produce sterile males.

Figure 5:
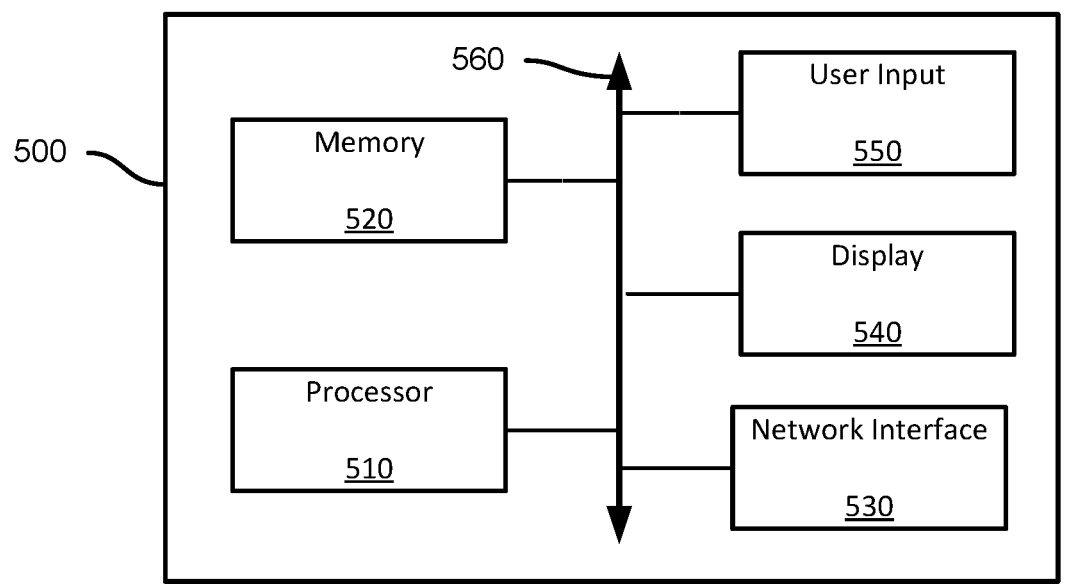
FIG. 5 depicts an example computing device for automated mass rearing systems according to this disclosure.

Referring now to FIG. 5, FIG. 5 shows an example computing device 500 suitable for acceleration of online certificate status checking with an Internet hinting service. The example computing device 500 may be suitable for use as any of the computing devices of FIGS. 1 and 2. The computing device 500 includes a processor 510, a memory 520, a network interface 530, a display 540, and one or more user input device 550. Each of these components is in communication with the other components via one or more communications buses 560. Suitable network interfaces 330 may employ wired or wireless network interfaces, such as wired Ethernet, 10-, 100-, 1000-base T, or 10GigE; FireWire 1394, USB, fiber optic, wireless Ethernet, including 802.11 a, g, b, n, or ac standards. In one example, the network interface 330 can communicate using Radio Frequency (RF), Bluetooth, CDMA, TDMA, FDMA, GSM, Wi-Fi, satellite, or other cellular or wireless technology.

While some examples of methods and systems herein are described in terms of software executing on various machines, the methods and systems may also be implemented as specifically-configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs for editing an image. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. The phrase "based on" should be understood to be open-ended, and not limiting in any way, and is intended to be interpreted or otherwise read as "based at least in part on," where appropriate. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present. Additionally, conjunctive language such as the phrase "at least one of X, Y, and Z," unless specifically stated otherwise, should also be understood to mean X, Y, Z, or any combination thereof, including "X, Y, and/or Z."

What is claimed is:

1. An automated insect rearing system comprising:
an insect dispensing station having a first horizontal surface;
an insect dispenser comprising an insect container and an insect dispensing vessel, a first end of the insect dispensing vessel coupled to a first orifice defined in the insect container and a second end of the insect dispensing vessel movable to be proximate to the first horizontal surface to dispense one or more insects from the insect container at the first horizontal surface;
a food dispensing station having a second horizontal surface;
a food dispenser comprising a food container and a food dispensing vessel, a first end of the food dispensing vessel coupled to a second orifice defined in the food container and a second end of the food dispensing vessel movable to be proximate to the second horizontal surface to dispense food from the food container at the second horizontal surface; and a robotic storage system comprising at least one robotic arm and a shelf, the robotic arm configured to transfer a rearing container from the second horizontal surface to the shelf.

2. The system of claim 1, wherein the first horizontal surface and the second horizontal surface are the same surface.

3. The system of claim 1, wherein the insect dispenser includes an egg dispenser or a larvae dispenser, wherein the one or more insects includes insect eggs or insect larvae, wherein the insect eggs comprises mosquito eggs, and wherein the insect larvae comprises mosquito larvae.

4. The system of claim 1, wherein the robotic storage system comprises a plurality of shelves.

5. The system of claim 1, wherein the robotic storage system further includes one or more temperature controls and one or more lighting controls, the one or more temperature controls configured to adjust a temperature surrounding the rearing container and the one or more lighting controls configured to adjust a lighting surrounding the rearing container.

6. The system of claim 1, further comprising:
a draining station comprising at least a third horizontal surface, a blade, and an emergence vessel, the blade movable to be proximate to the third horizontal surface to cut open the rearing container placed onto the third horizontal surface to release contents of the rearing container into the emergence vessel.

7. The system of claim 6, wherein the disposable container creation system further comprises a heat sealer configured to seal at least portions of an upper layer and a bottom layer of the heat moldable material to form the rearing container, and wherein the form filling machines comprises a post creation machine, the post creation machine configured to create one or more posts in the layer of the heat moldable material.

8. The system of claim 1, further comprising:
a computing device comprising a user interface, the user interface configured to manage a movement of one or more trays holding the rearing container, and wherein the user interface is further configured to schedule one or more actions to be performed on the rearing container.

9. The system of claim 1, wherein the robotic arm comprises a gripper arm with a vacuum cup for grasping the rearing container.

10. The system of claim 7, further comprising:
a disposable container creation system comprising at least a spool of heat moldable material and a form filling machine, the form filling machine configured to create one or more indentations in a layer of the heat moldable material.

11. The system of claim 1, wherein the one or more insects is dispensed from the insect container to the rearing container, and wherein the food is dispensed from the food container to the rearing container.

12. The system of claim 1, further comprising:
a monitor system comprising a computing device and one or more sensors, the one or more sensors configured to monitor the one or more insects in the rearing container, and the computing device configured to adjust one or more parameters associated with the rearing container responsive to data obtained from the monitoring.

13. The system of claim 1, further comprising:
an inspection station having a third horizontal surface and one or more sensors, the one or more sensors configured to collect data on the rearing container while the rearing container is placed on the third horizontal surface.

14. The system of claim 1, further comprising:
a water dispensing station having a third horizontal surface; and
a water dispenser comprising a water container and a water dispensing vessel, a first end of the water dispensing vessel coupled to a first orifice defined in the water container and a second end of the water dispensing vessel movable to be proximate to the third horizontal surface to dispense water from the water container at the third horizontal surface into the rearing container.

15. A method of rearing insects, the method comprising:
dispensing, by an insect dispenser of an automated rearing system, one or more insects into a rearing container;
dispensing, by a food dispenser of the automated rearing system, food for the one or more insects into the rearing container;
transporting, by one or more robotic arms of the automated rearing system, the rearing container to a storage area of the automated rearing system; and
monitoring, by one or more processors coupled to the automated rearing system, development of the one or more insects in the rearing container using one or more sensors in the storage area of the automated rearing system.

16. The method of claim 15, wherein the one or more robotic arms of the automated rearing system includes a gripper arm, and wherein the one or more robotic arms transports the rearing container via a vacuum cup coupled to the gripper arm.

17. The method of claim 15, further comprising:
creating, by the automated rearing system, the rearing container for housing the one or more insects; and
dispensing, by a water dispenser, water into the rearing container.

18. The method of claim 17, further comprising:
draining, using a water pump coupled to the automated rearing system, the water from the rearing container;
refilling, by the water dispenser, additional water into the rearing container to replace at least a portion of the water drained from the rearing container; and
pumping, using an air pump coupled to the automated rearing system, additional air into the rearing container.

19. The method of claim 17, wherein creating the rearing container for housing the one or more insects includes:
dispensing a bottom layer and a top layer of heat moldable material from a spool of the heat moldable material; and
partially sealing, using a heat sealer, edges of the bottom layer and the top layer of the heat moldable material.

20. The method of claim 15, further comprising:
adjusting an amount of food that is dispensed into the rearing container based on data obtained from the monitoring.

21. The method of claim 15, further comprising:
receiving input specifying an adjustment to one or more parameters associated with the rearing container; and
updating an amount of food to dispense into the rearing container based on the received input, wherein the updated amount of food is automatically dispensed into the rearing container one or more times during a rearing process of the one or more insects.

22. The method of claim 15, wherein the one or more insects includes at least one of insect eggs or insect larvae, wherein the insect eggs is mosquito eggs and the insect larvae is mosquito larvae, and wherein the method further comprises:

draining contents of the rearing container into an emergence vessel, wherein the contents include mosquito pupae evolved from the mosquito larvae.

23. The method of claim 15, further comprising:

presenting a user interface on a display of a computing device;

receiving a selection of one or more rearing containers; and receiving adjustments to one or more parameters associated with the selected rearing containers.

24. The method of claim 23, wherein the one or more parameters comprise one or more of an environment parameter or an action to be taken on the selected rearing containers.

25. The method of claim 24, wherein the action comprises one of dispensing food or water into the container, draining water from the container; draining insect larvae or insect pupae from the container, or transporting the selected containers to another position within the automated rearing system.

26. The method of claim 15, further comprising:

receiving sensor signals from the one or more sensors, wherein the monitoring is based on the received sensor signals.

27. The method of claim 15, further comprising:

detecting, via the one or more sensors, a change associated with contents of the rearing container; and adjusting one or more parameters associated with the rearing container in response to the detected change.

28. The method of claim 15, further comprising:

detecting an environmental condition associated with the rearing container;

in response to determining the environmental condition exceeds a predetermined setting, modifying an environmental control based on the environmental condition and the predetermined setting.

29. The method of claim 28, wherein the environmental condition comprises one or more of a temperature, a humidity, or a lighting condition, and wherein the environmental control comprises one or more of a temperature control, a humidity control, or a lighting control.

30. The method of claim 15, further comprising:

receiving, by a computing device, a selection of the rearing container;

in response to the selection:

retrieving and transporting, by one of the one or more robotic arms, the rearing container from the storage area to an inspection station.

31. The method of claim 15, further comprising:

determining, by a computing device, that the rearing container is in a low food condition;

in response to the low food condition:

retrieving and transporting, by one of the one or more robotic arms, the rearing container from the storage area to a dispensing station;

dispensing, by the food dispenser, food into the rearing container; and transporting, by one of the one or more robotic arms, the rearing container from the dispensing station to the storage area.

32. The method of claim 15, further comprising:

determining, by a computing device, that the rearing container is in a low water quality condition;

in response to the low water quality condition:

opening a drainage passage of the rearing container to drain water from the rearing container;

retrieving and transporting, by one of the one or more robotic arms, the rearing container from the storage area to a dispensing station;

dispensing water into the rearing container; and transporting, by one of the one or more robotic arms, the rearing container from the dispensing station to the storage area.

* * * * *